United States Patent [19]

Cure

[11] 4,037,478

[45] July 26, 1977

[54] DEVICE FOR COLLECTING SAMPLES OF MOLTEN METAL

[75] Inventor: Omer P. Cure, Diepenbeek, Belgium

[73] Assignee: Electro-Nite Co., Philadelphia, Pa.

[21] Appl. No.: 723,360

[22] Filed: Sept. 15, 1976

[51] Int. Cl.$^2$ ............................................. G01N 1/12
[52] U.S. Cl. ........................... 73/425.4 R; 73/DIG. 9
[58] Field of Search ..................... 73/425.4 R, DIG. 9

[56] References Cited

U.S. PATENT DOCUMENTS

| 3,646,816 | 3/1972 | Hance | 73/425.4 |
| 3,805,621 | 4/1974 | Falk | 73/425.4 |
| 3,859,857 | 1/1975 | Falk | 73/425.4 |

*Primary Examiner*—S. Clement Swisher
*Attorney, Agent, or Firm*—Seidel, Gonda & Goldhammer

[57] ABSTRACT

The entrance on a sampling device for molten metal is defined in part by a tube made from a deoxidizing agent such as aluminum. The tube melts as a sample of molten bath passes therethrough to a collecting chamber so that all portions of the sample are deoxidized uniformly.

12 Claims, 4 Drawing Figures

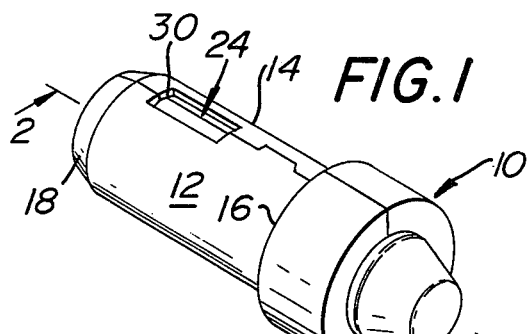
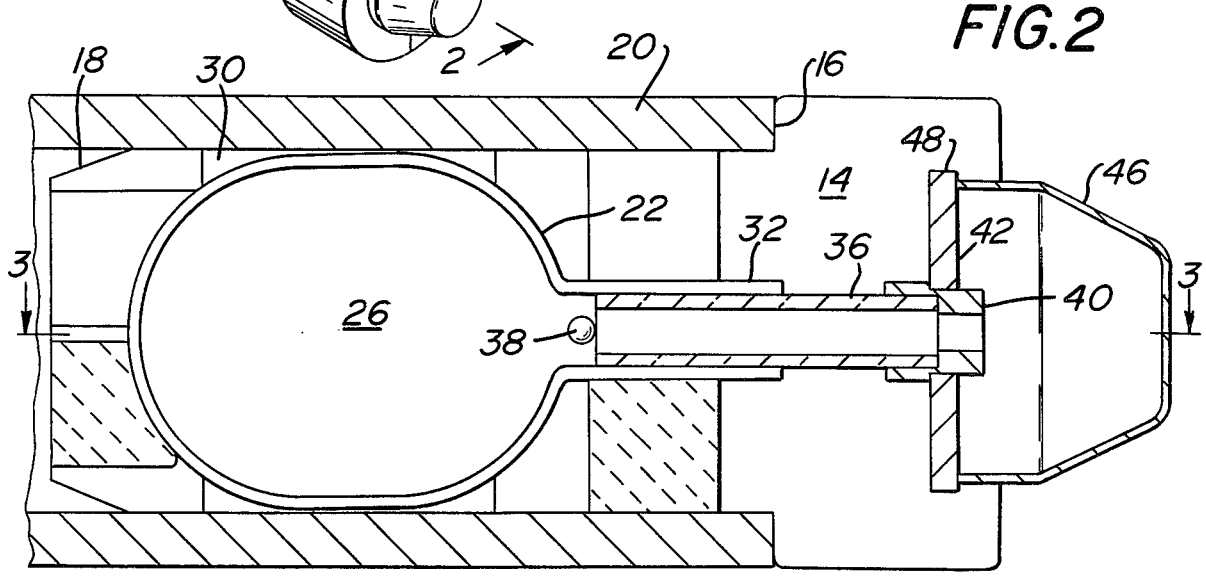
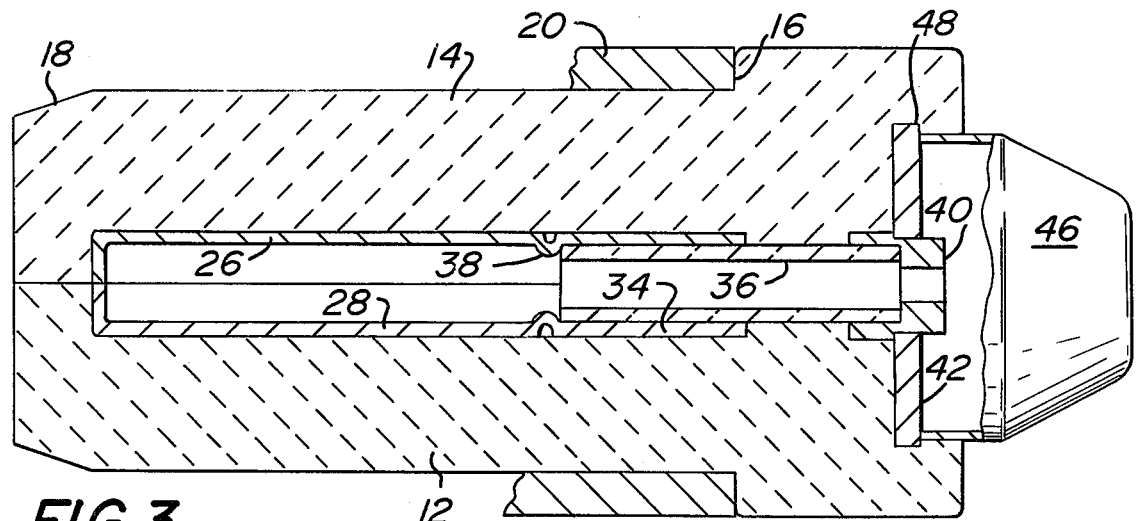
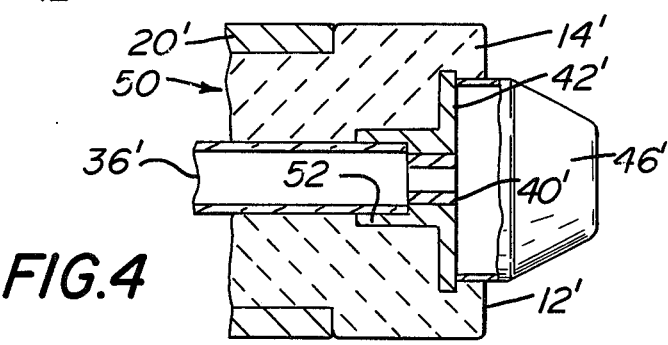

DEVICE FOR COLLECTING SAMPLES OF MOLTEN METAL

BACKGROUND

U.S. Pat. Nos. 3,369,406; 3,646,816 and 3,805,621 are considered representative of the prior art. Numerous devices for collecting samples from a bath of molten metal have been proposed heretofore. One of the problems involved in such devices is the uneven distribution of a deoxidizing agent in the sample.

It is common to provide a deoxidizing agent, such as aluminum in the shape of wire or a tube, along the entrance of or in a sampling device for contact with the molten metal sample. When the molten metal enters the sampling device, the deoxidizing agent is almost immediately melted away so as to result in the initial portion of the sample being deoxidized whereas the last portion of the sample to enter the chamber has virtually no deoxidation.

Another problem involved in using prior art devices relates to a loss of the sample when the sampling device is withdrawn from the bath. In this regard, the entrance to the sampling chamber is below the sampling chamber and the sampling device is upright when introduced into the molten bath. Thus, it has been noted that withdrawal of the sampling device from the bath results in a portion of the sample returning to the bath. Another problem with the prior art relates to disassembly of the components to attain access to the specimen. The above and other disadvantages of the prior art are solved by the present invention.

SUMMARY OF THE INVENTION

The device for collecting a sample of molten metal in accordance with the present invention includes a body having a chamber therein. A vessel is provided in said chamber. A filling conduit is supported by the body and has one end communicating with said vessel. A tube of deoxidizing material is supported by the body adjacent the other end of said conduit. A metal ring having a melting temperature greater than that of the deoxidizing tube is coupled to the outer periphery of said tube.

In a preferred embodiment of the present invention, the body of the device is split longitudinally and temporarily bonded together during assembly with a material such as a hot melt adhesive which will be rendered ineffective by the temperature of a bath. When the body is removed from its manipulating support such as a cardboard tube, the body on impact will separate into the two discrete halves. At the same time, the sampling retrieval vessel will separate into two halves, a filling conduit will shatter, and the specimen will separate from the other components. In this manner, retrieval of the sample is attained merely by causing the body to fall a distance of several feet onto a concrete floor.

It is an object of the present invention to provide a device for collecting a sample of molten metal which is constructed to assure uniform deoxidization of the sample.

It is another object of the present invention to provide a device for collecting a sample of molten metal which enables the sample to be easily retrieved without disassembly of any components.

Other objects will appear hereinafter.

For the purpose of illustrating the invention, there is shown in the drawings a form which is presently preferred; it being understood, however, that this invention is not limited to the precise arrangements and instrumentalities shown.

FIG. 1 is a perspective view of a device for collecting samples of molten metal in accordance with the present invention.

FIG. 2 is a sectional view taken along the line 2—2 in FIG. 1, with the device mounted in one end of a support such as a cardboard tube.

FIG. 3 is a sectional view taken along the line 3—3 in FIG. 2.

FIG. 4 is a view similar to FIG. 3 but on a smaller scale and showing an alternative embodiment of the present invention.

Referring to the drawing in detail, wherein like numerals indicate like elements, there is a device in accordance with the present invention designated generally as 10.

The device 10 includes a body made from a refractory material which is inexpensive such as foundry sand. The body of the device 10 is preferably made with mating halves 12 and 14. An enlarged head on one end of the body defines a shoulder 16 for contact with one end of a support such as cardboard tube 20. The other end of the body is provided with a taper 18 to facilitate the ease of introduction of the device 10 into the cardboard tube 20.

The two halves, prior to introduction into the tube 20, are retained in assembled relationship by use of spots of adhesive such as a hot melt adhesive on the juxtaposed faces of the body halves 12 and 14. Such adhesive facilitates the ease of handling and assembling of the device 10 into the cardboard tube 20. The outer diameter of the device 10 is such that it is a slight force-fit with respect to the inner diameter of tube 20. In this manner, the tube 20 may be held in an upright position and the device 10 will not fall out or separate even though the adhesive is no longer effective. It will be noted that the head on the immersion end of the device 10 is of substantially the same diameter as the outer diameter of tube 20.

The body of the device 10 is provided internally with a chamber 22 within which is disposed a vessel 24. As shown more clearly in FIG. 1, the device 10 is provided with an opening 30 at the parting line of the body halves whereby the vessel 24 is visible. The vessel 24 is preferably a metal vessel made from separable halves 26 and 28. The halves 26 and 28 have mating semi-circular stems 32, 34, respectively.

A conduit 36 having a smooth inner peripheral surface and made from a frangible refractory material such as quartz is provided. One end of the conduit 36 communicates with the interior of the vessel 24 and abuts against the limit stop dimples 38. A tube 40 of a deoxidizing material such as aluminum may be coaxial with the other end of conduit 36. The inner diameter of tube 40 is less than the inner diameter of conduit 36 but has a thicker wall than conduit 36. Tube 40 has an extension surrounding the conduit 36.

A metal ring 42 is coupled to the tube 40. Preferably, ring 42 is force-fit onto the outer periphery of tube 40 and abuts against a shoulder on the tube extension. Ring 42 is made from a material such as iron or steel and has a melting temperature substantially higher than the melting temperature of aluminum. A cap 46 has its open end in contact with the ring 42 and is disposed along the longitudinal axis of the device 10. The body halves 12 and 14 are notched for receiving the periphery of ring 42 to thereby position tube 40 in a predetermined position against one end of the conduit 36. Cap 46 is made from a low temperature melting material or is thin walled and merely provides protection when the device 10 is introduced through a slag layer.

The manner in which the devices of the generally type involved herein are utilized is well known to those skilled in the art. Hence, only a brief discussion is deemed necessary. The tube 20 is grasped by an operator and the immersion end thereof containing the device 10 is introduced through the slag into a bath of molten metal. The cap 46 is melted during passage through the slag. Molten metal flows through tube 40, through conduit 36, into the vessel 24. Any air in the vessel 24 is expelled through the gap between the mating halves and through the opening 30 into the interior of the cardboard tube 20.

As the molten metal flows through the tube 40, the tube 40 is melted along its inner peripheral surface thereby deoxidizing the molten metal. The tube 40 has sufficient mass whereby it does not melt away until the vessel 24 and 36 have been filled with molten metal. Hence, even the last portion of the molten metal forming a part of the sample to be retrieved will be deoxidized.

The ring 42 acts as a cooling body for the portion of the tube 40 which remains after a complete sample has been obtained. It has been discovered that the ring 42 has a cooling effect on the tube 40 whereby none of the sample flows out of the conduit 46 upon withdrawal of the device 10 from the bath.

Since the adhesive retaining the body halves 12 and 14 together is no longer effective, the force fit of the device 10 within the cardboard tube 20 is the only force retaining the device 10 in an assembled relationship. Application of force for ejecting the device 10 from the immersion end of the tube 20 may be accomplished in any one of a wide variety of manners. Upon such ejection, the device 10 is permitted to fall at least several feet onto a concrete floor. Upon impact with the floor, the body of the device 10 separates along the parting line, the vessel 24 separates into two halves and the conduit 36 breaks or is easily broken to thereby expose the specimen which has the general shape of a lollipop with flat sides, a stem and a generally oval configuration.

In FIG. 4, there is illustrated another embodiment of the present invention which is identical with that described above except as will be mae clear hereinafter. Hence, corresponding elements are provided with corresponding primed numerals. The device designated as 50 differs from the embodiment set forth above in that the ring 42' has an extension or boss 52 which is telescoped over the inlet end of the conduit 36'. The tube 40' of deoxidizing material is force-fit into the ID of the ring 42'.

Thus, it will be seen that the device of the present invention is structurally interrelated in a manner so as to readily separate into components to facilitate access to the specimen while at the same time will provide a specimen which is uniformly homogeneous.

The present invention may be embodied in other specific forms without departing from the spirit or essential attributes thereof and, accordingly, reference should be made to the appended claims, rather than to the foregoing specification as indicating the scope of the invention.

It is claimed:

1. A device for collecting a sample of molten metal comprising a non-metallic body having a chamber therein, a vessel in said chamber, a filling conduit supported by said body, said conduit having one end communicating with said vessel, a tube of deoxidizing material supported by said body adjacent the other end of said conduit and communicating therewith, and a metal ring coupled to the outer diameter of said tube, said metal ring having a melting temperature greater than the melting temperature of said tube.

2. A device in accordance with claim 1 wherein said conduit is made from a frangible material, said vessel being a metallic vessel comprised of mating portions which are readily separable.

3. A device in accordance with claim 1 wherein said metal ring is force-fit to the outer peripheral surface of said tube, said tube being coaxial with respect to said conduit.

4. A device in accordance with claim 1 wherein a portion of said metal ring surrounds the inlet end of said conduit.

5. A device in accordance with claim 1 wherein a portion of said tube surrounds the inlet end of said conduit.

6. Sampling apparatus comprising an expendable support tube having an immersion end, a sampling device mounted in said immersion end, said device including a non-metallic body having a chamber therein, a vessel separable into components, said vessel being disposed with said chamber, a filling conduit supported by said body, said conduit having one end communicating with said vessel, a tube of deoxidizing material supported by said body, said deoxidizing tube communicating directly with the other end of said conduit, a metal ring having a melting temperature greater than the melting temperature of said deoxidizing tube, said metal ring being secured to the outer periphery of said deoxidizing tube and having a mass greater than the mass of said deoxidizing tube.

7. Apparatus in accordance with claim 6 wherein said body is comprised of several components force fit into said immersion end of said support tube in a manner so that the body may be separated into its components after retrieving a sample by withdrawal of said body from said support tube.

8. Apparatus in accordance with claim 6 wherein said body has a radially disposed surface overlying at least a portion of a peripheral surface of said ring to prevent movement of said ring in an axial direction.

9. Apparatus in accordance with claim 6 wherein said body is comprised of two halves made from a refractory material and held in assembled relationship by a bonding agent which will be rendered ineffective when the device is immersed in a bath of molten metal.

10. Sampling apparatus comprising an expendable support tube having an immersion end, a sampling device force fitted in said immersion end, said device including a refractory body having a chamber therein, said body being split longitudinally and held together by a hot melt adhesive, a flat metal vessel separable into components, said vessel being disposed with said chamber, a smooth bore conduit supported by said body, said conduit having one end communicating with said vessel, a tube of deoxidizing material supported by said body so as to be coaxial with said conduit, said deoxidizing tube communicating directly with the other end of said conduit, a ring capable of withstanding greater temperatures than said deoxidizing tube, said ring being secured to the outer periphery of said deoxidizing tube with major faces of the ring being radially disposed and said ring having a mass greater than the mass of said deoxidizing tube, and an expendable protective cap member for protecting said deoxidizing tube.

11. Sampling apparatus comprising an expendable support tube having an immersion end, a sampling device removably in said immersion end and projecting therefrom, said device including a nonmetallic refractory body, means defining a flat vessel in said body, a filling conduit supported by said body, said conduit having one end communicating with said vessel, a tube of deoxidizing material supported by said body so as to be coaxial with said conduit and communicating directly with the other end of said conduit, a ring capable of withstanding greater temperatures than said deoxidizing tube, said ring being fixedly secured to the outer periphery of said deoxidizing tube and projecting radially outwardly therefrom, said ring having a mass greater than the mass of said deoxidizing tube, and an expendable member for protecting said deoxidizing tube until said device is immersed in a bath of molten metal.

12. Sampling apparatus in accordance with claim 11 wherein said body is split longitudinally and held together by an agent which is rendered ineffective by a bath of molten metal.

* * * * *